United States Patent [19] [11] 4,220,749
Reichmann et al. [45] Sep. 2, 1980

[54] PROCESS FOR THE PRODUCTION OF MODIFIED POLYISOCYANATES

[75] Inventors: Wolfgang Reichmann, Duesseldorf; Klaus König; Heinz-Georg Nordmann, both of Leverkusen, all of Fed. Rep. of Germany

[73] Assignee: Bayer Aktiengesellschaft, Leverkusen, Fed. Rep. of Germany

[21] Appl. No.: 917,765

[22] Filed: Jun. 21, 1978

[30] Foreign Application Priority Data

Jul. 6, 1977 [DE] Fed. Rep. of Germany ....... 2730513

[51] Int. Cl.² .................. C07C 27/24; C08G 18/72
[52] U.S. Cl. .................................... 528/44; 521/155; 528/73; 528/81; 544/58.4; 544/168; 544/386; 546/245; 548/200; 548/236; 548/341; 260/326.4; 260/453 AB; 560/169
[58] Field of Search ............ 260/453 AB, 326.4; 546/245; 528/44, 81

[56] References Cited

U.S. PATENT DOCUMENTS

| | | | |
|---|---|---|---|
| 3,392,183 | 7/1968 | Windemuth et al. | 260/453 AB |
| 3,647,848 | 3/1972 | Wagner et al. | 260/453 AB |
| 3,862,973 | 1/1975 | Dietrich et al. | 260/453 AB |
| 3,903,127 | 9/1975 | Wagner et al. | 260/453 AB |
| 4,001,290 | 1/1977 | Wagner et al. | 260/453 AB |

*Primary Examiner*—Dolph H. Torrence
*Attorney, Agent, or Firm*—Gene Harsh; Lawrence S. Pope

[57] ABSTRACT

This invention relates to a new process for the production of organic polyisocyanates containing polyuret groups, to polyisocyanates obtainable by this process and to the use of the products obtained by the process as an isocyanate component in the production of polyurethane plastics.

14 Claims, No Drawings

PROCESS FOR THE PRODUCTION OF MODIFIED POLYISOCYANATES

BACKGROUND OF THE INVENTION

Polyisocyanates containing biuret groups are known and are used in practice as starting materials for high-grade, light-stable lacquers. They may be produced, for example, from diisocyanates and water (DT-AS No. 1,101,394 and U.S. Pat. No. 3,201,372), hydrogen sulphide (DT-AS No. 1,165,580), formic acid (DT-AS No. 1,174,760 and U.S. Pat. No. 3,392,183), tertiary alcohols (DT-AS Nos. 1,543,178 and 1,931,055 and U.S. Pat. No. 3,358,010); monoamines (DT-OS No. 2,308,015 and U.S. Pat. No. 3,903,127) or polyamines (DT-OS No. 2,261,065 and U.S. Pat. No. 3,903,126).

These conventional processes for the production of biuret polyisocyanates are attended by a number of disadvantages.

Thus, in most conventional processes, amino groups are initially formed from some of the isocyanate groups and further reacted with excess diisocyanate to form biuret polyisocyanates by way of the corresponding diisocyanate ureas. Conversion of the isocyanate groups into amino groups is always accompanied by the formation of gaseous secondary products, such as carbon dioxide, carbon monoxide, carbon sulphoxide or olefin, the elimination of which may give rise to waste-gas problems. In the heterogeneous reaction of diisocyanates with water, there is the additional danger of insoluble polyureas being formed. These insoluble polyureas may only be separated off with difficulty. The reaction of diisocyanates with tertiary alcohols which is commercially used for the production of biuret polyisocyanates is attended by the further disadvantage that relatively high temperatures are required for splitting the urethanes to convert the isocyanate groups into amino groups. A further disadvantage is the fact that, in these processes, some of the isocyanate groups of the diisocyanate used as starting material are destroyed to form amino groups.

Although, according to DT-OS No. 2,261,065 and U.S. Pat. No. 3,903,126, the direct reaction of polyamines with diisocyanates leads to biuret polyisocyanates without any elimination of volatile secondary products and without any conversion of isocyanate groups into amino groups, considerable practical difficulties arise in this process, particularly in cases where commercially readily available starting materials, such as hexamethylene diamine and hexamethylene diisocyanate, are used because, on account of the high reactivity of the amino groups to the isocyanate groups, the tendency for insoluble polyureas to be formed is very considerable, with the result that in most cases the reaction has to be completed by after-heating the reaction mixture at elevated temperatures for an uneconomically long period, which results in a considerable deterioration in the properties of the end products, particularly the natural color thereof.

In all conventional processes, diisocyanates are converted into biuret polyisocyanates with the disadvantages referred to above. At the same time, there is no further reaction to form polyuret polyisocyanates.

Accordingly, an object of the present invention is to provide a new process by which it is readily possible to produce high-quality modified polyisocyanates combining the advantages of biuret polyisocyanates and which is not attended by any of the above-mentioned disadvantages of conventional processes.

Surprisingly, it has been found that this object may be achieved by reacting certain organic monoamines described in more detail below with excess quantities of certain diisocyanates described in more detail below under particular reaction conditions which are described in more detail below.

SUMMARY OF THE INVENTION

The present invention relates to a process for the production of modified organic polyisocyanates containing triuret or higher polyuret groups, wherein primary or secondary monoamines are reacted with excess quantities of organic diisocyanates with the formation of triuret or higher polyuret groups and with incorporation into the product of the residue of the amine which is inert to the reaction. Proton-eliminating acids are present as catalysts in the process.

The present invention also relates to the preferred polyisocyanate compounds obtainable by this process which correspond to the following general formula:

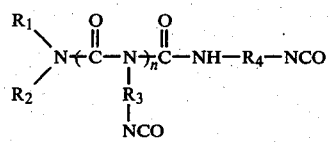

wherein

R$_1$ and R$_2$, which may be the same or different, each represents an aliphatic hydrocarbon radical containing from 1 to 20 carbon atoms or a cycloaliphatic hydrocarbon radical containing from 4 to 20 carbon atoms or the two radicals together with the nitrogen atom may form a 5- or 6-membered heterocyclic ring optionally containing further hetero atoms such as i.e. nitrogen, oxygen or sulphur;

R$_3$ and R$_4$, which may be the same or different, each represents an aliphatic or cycloaliphatic hydrocarbon radical containing from 4 to 20 carbon atoms; and n represents a number from about 2 to 8.

Furthermore, the present invention also relates to the use of the modified polyisocyanates obtainable by the process according to the present invention as an isocyanate component in the production of polyurethane plastics by the isocyanate polyaddition process.

DETAILED DESCRIPTION OF THE INVENTION

Starting materials for the process according to the present invention are any organic compounds which contain a primary or secondary amino group, but which are otherwise inert under the conditions of the process according to the present invention. Such compounds include:

1. Aromatic monoamines containing primary or secondary amino groups, for example aniline, N-methyl aniline, N-ethyl aniline or N-butyl aniline. However, such aromatic amines are less preferred by comparison with the amines exemplified below.

2. Monoamines corresponding to the following general formula:

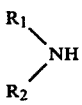

wherein

R₁ and R₂ are as defined above and, in addition, R₁ may also represent hydrogen.

It is preferred to use those monoamines corresponding to the above general formula wherein R₁ and R₂, which may be the same or different, each represents an aliphatic hydrocarbon radical containing from 1 to 4 carbon atoms, in addition to which R₁ may also represent hydrogen, or wherein R₁ and R₂, together with the nitrogen atom, form a piperidine radical.

Particularly preferred starting materials are the secondary monoamines corresponding to the above definition. It is also possible to use mixtures of the above-mentioned amines.

The following are specific examples of monoamines which are preferably used in or rather particularly suitable for use in the process according to the present invention: methylamine, ethylamine, propylamine, isopropylamine, isomeric butylamines, pentylamine, hexylamine, cyclohexylamine, dodecylamine, dimethylamine, diethylamine, dipropylamine, dibutylamine, bis-(2-ethylhexyl)-amine, N-methyl cyclohexylamine, N-ethyl cyclohexylamine, N-methyl octadecylamine, pyrrolidine, and piperidine.

In the practical application of the process according to the present invention, modified polyisocyanates containing triuret or higher polyuret groups, in which the residue of the amine that is inert to the reaction is incorporated, are formed from the exemplified monoamines and the diisocyanates exemplified below.

This reaction takes place by way of the intermediate stages of the compounds containing urea groups which are formed from the amines and the diisocyanates or of compounds containing biuret groups which are formed from the compounds containing urea groups by reaction with more diisocyanate. Accordingly, intermediate stages are the monourea monoisocyanates which are formed by the addition of 1 mol of amine and 1 mol of diisocyanate or even bisureas formed from 2 mols of amine and 1 mol of diisocyanate or the biuret polyisocyanates which are formed from these with more diisocyanate. A logical consequence of this is, of course, the fact that these intermediate products produced, for example, in a separate operation from the exemplified monoamines and the isocyanates exemplified below may also be used as starting material in a modification of the process according to the present invention. The way in which these intermediate products are produced is, of course, unimportant. Thus, it would, of course, also be possible to use as starting material in the process according to the present invention the reaction product containing urea groups of 1 mol of hexamethylene-biscarbamic acid chloride and 2 mols of monoamine which corresponds to the reaction product containing urea groups of 1 mol of hexamethylene diisocyanate and 2 mols of the same monoamine.

Diisocyanates suitable for use in the process according to the present invention include any organic diisocyanates which, apart from the isocyanate groups, do not contain any other groups that are reactive under the reaction conditions of the process according to the present invention. It is possible to use both the classic aromatic diisocyanates of polyurethane chemistry, such as 2,4-diisocyanatotoluene, 2,6-diisocyanatotoluene, mixtures of these isomers or 4,4'-diisocyanatodiphenyl methane. However, it is preferred to use diisocyanates containing aliphatically and/or cycloaliphatically bound isocyanate groups, particularly those in which the two isocyanate groups are attached through aliphatic hydrocarbon radicals containing from 4 to 12 carbon atoms or through cycloaliphatic hydrocarbon radicals containing from 4 to 15 carbon atoms, the aliphatic or cycloaliphatic hydrocarbon chains optionally being interrupted or substituted by ester groups, such as: 1,4-diisocyanatobutane, 1,6-diisocyanatohexane, 2,4,4-trimethyl-1,6-diisocyanatohexane, 1,11-diisocyanatoundecane, 3-isocyanatomethyl-3,5,5-trimethyl cyclohexyl isocyanate, 4,4'-cyclohexane diisocyanate, 4,4'-dicyclohexyl methane diisocyanate, 1,2-bis-(isocyanatomethyl)-cyclobutane or 6-isocyanatocaproic acid-2-isocyanatoethyl ester. It is preferred to use hexamethylene diisocyanate.

It is, of course, also possible to use diisocyanate mixtures, in which case a urea or biuret is initially produced, for example, from a diisocyanate with a monofunctional amine, the urea or biuret thus produced forming polyurea with another diisocyanate.

Whereas the reaction of amines with diisocyanates to form the corresponding ureas or biurets belongs to the prior art, there has hitherto been no commercially workable process which enables the addition reaction taking place between amine and isocyanate to be continued beyond the intermediate stage of the corresponding biurets. This is attributable to the poor reactivity of the biurets with respect to organic diisocyanates which may be overcome by using suitable catalysts. Now, according to the present invention, the further reaction of monoamines with excess diisocyanate beyond the urea and biuret stage to form polyurets is carried out in the presence of catalysts.

The catalysts used in accordance with the present invention are proton-eliminating strong acids which react with isocyanates, particularly with aliphatic or cycloaliphatic isocyanates, to form a mixed acid anhydride, the carbamic acid corresponding to the isocyanate and the proton-eliminating acid representing the acids of the mixed acid anhydride. Thus, acids such as those of the formula HX (X represents acid residue after elimination of the proton), which are suitable for use in the process according to the present invention, react with isocyanates Y—NCO to form adducts of the formula Y—NH—CO—X which may be regarded as a mixed anhydride of the carbamic acid Y—NH—COOH and the acid HX.

Examples of suitable acids include hydrohalic acids, such as hydrogen fluoride, hydrogen chloride, hydrogen bromide or hydrogen iodide, chlorosulphonic acid, fluorosulphonic acid, sulphuric acid, alkane sulphonic acids, such as methane sulphonic acid, or perhalogenated alkane sulphonic acids, such as trifluoromethane sulphonic acid. Hydrogen chloride is the acid preferably used in the process according to the present invention.

Instead of using the acids, it is, of course, also possible in the process according to the present invention to use both the ammonium salts corresponding to the acids with the amines used as starting material or the mixed carbamic acid anhydrides corresponding to the acids, particularly carbamic acid chloride, with the diisocyanates used as starting material or any other isocyanate. In general, the catalysts may be used in quantities of from about 0.001 to 10%, by weight, preferably from about 0.01 to 1.0%, by weight, based on the total weight of the reactants.

The process according to the present invention may be carried out at relatively low temperatures of from about 0° to 140° C., particularly where the exemplified acids are used as catalysts, the reaction leading beyond the biuret polyisocyanate stage to form reaction products containing triuret and polyuret groups generally taking place at temperatures of from about 90° to 140° C. Accordingly, the catalysis according to the present invention with the acids exemplified above enables isocyanate addition products containing polyuret groups to be produced under mild reaction conditions from organic diisocyanates and organic monoamines or from compounds containing urea groups or biuret groups formed from monoamines and diisocyanates. Where the process according to the present invention is carried out with monoamines as starting materials, no readily volatile secondary products are formed by virtue of the mild reaction conditions. In particular, even where primary monoamines are used as starting materials, no monoisocyanates corresponding to these monoamines are formed. Accordingly, the residue of the monoamines which is inert with respect to the reaction according to the present invention always forms part of the products according to the present invention.

Where the process according to the present invention is carried out with monoamines as starting materials, the monoamines and the diisocyanates are generally used in quantitative ratios which correspond to an NCO/NH-molar ratio of from about 5.5:1 to 100:1, preferably from about 6:1 to 30:1. In cases where starting materials containing urea groups, i.e. monourea monoisocyanates or bisureas formed from monoamines and diisocyanates, are used, corresponding quantitative ratios apply, although in this case allowance has to be made for the fact that the above-mentioned starting materials containing urea groups already contain monoamines and diisocyanates in a molar ratio of about 1:1 and 2:1, respectively. These monoamines and diisocyanates present in the form of the starting materials containing urea groups enter into the calculation of the amine:diisocyanate quantitative ratio. The same considerations also apply where the starting materials used contain biuret groups, such as are formed by reacting the above-mentioned intermediate products containing urea groups with more diisocyanate.

The process according to the present invention is generally carried out as follows:

The diisocyanate is initially introduced into a suitable reaction vessel, followed by addition of the monoamine at temperatures of from about 0° to 100° C. The NCO/NH-molar ratio generally amounts to from about 6:1 to 30:1. Solid amines are added from a heated dropping funnel, while liquid amines are added from a normal dropping funnel. Gaseous amines are introduced into the diisocyanate optionally together with an inert gas stream. The corresponding ureas are spontaneously formed. Where primary amines are used, they are generally precipitated to begin with and then enter into solution through further reaction to form biurets at from about 80° to 120° C. Where secondary amines are used, the reaction generally stops in the absence of a catalyst at the stage of the ureas which, in general, are not completely soluble in excess diisocyanate. A catalyst may be added at any stage of the reaction. For example, it may be initially introduced with the diisocyanate, added as an ammonium salt with the amines or only introduced on completion of the preliminary reaction which forms urea or biuret isocyanates. The reaction mixture is then heated to from about 90° to 140° C. and the progress of the reaction is followed by checking the reduction in the NCO-content. In cases where volatile catalysts, for example hydrogen chloride, are used, pressure may be applied in order to avoid possible losses of catalyst at elevated temperatures.

When the reduction in the NCO-content corresponds to the required "degree of polyuretization", i.e. when the required quantity of NCO-groups per amino group has been reacted, the reaction is terminated. This is simply done by cooling the reaction mixture to from about 20° to 50° C. The necessary reaction times are determined by the nature of the starting products, by the reaction temperature and, in particular, by the type and quantity of catalyst used. They generally amount to from about 1 to 20 hours, preferably from about 2 to 8 hours. On completion of the reaction, clear, colorless to pale yellowish reaction solutions are obtained.

The reactions are generally stopped at a time at which on average about 3 NCO-groups have been consumed in the process per amino group. By this time, the products have an average functionality of 3.5, taking the polymer homologues into consideration. However, it is also possible to obtain a higher "degree of polyuretization", i.e. to consume 4 and more NCO groups in the process per amino group. In that case, however, the viscosities of the products increase rapidly.

The catalyst is generally removed by distilling the reaction mixture in vacuo. In cases where hydrogen halides are used as catalysts, the catalyst may also be eliminated, particularly when used in relatively small amounts, by the addition of equimolar quantities of propylene oxide. It is also possible to remove the catalyst, for example, by thin layer evaporation if the crude isocyanate is to be freed from excess diisocyanate. The distillate of the thin-layer distillation process which, in addition to the diisocyanate, also contains the catalyst may be re-used as starting material.

In cases where it is intended to remove excess diisocyanate, this is generally done by thin-layer evaporation. However, excess diisocyanate may also be removed by extracting the reaction mixture with suitable solvents, such as hexane or heptane.

The crude isocyanates may be used as such. In most cases, however, they are freed from monomeric isocyanate components, preferably by thin-layer evaporation or by extraction. The monomer-free products are pale yellow oils or even solid resins; the NCO-content generally amounts to from about 10 to 22% by weight.

The process is eminently suitable for continuous operation. In such cases, several reaction vessels are arranged one behind the other in the form of a cascade. In the first reaction vessel, the starting products diisocyanate and monoamine are mixed at about 60° C. In the second reaction vessel, the catalyst is added at about 80° C. In the third and, optionally, further reaction vessels, the further reaction to form the triuret or higher polyisocyanate takes place at from about 90° to 140° C., the required "degree of polyuretization" being adjusted by controlling the temperature and residence times.

Excess diisocyanate and the catalyst are removed, for example, in a tubular coil evaporator combined with a following thin-layer evaporator. The distillates consisting of diisocyanate and catalyst are combined and returned to the process. The polyisocyanate is obtained as the thin-layer distillate residue.

As mentioned above, no monoisocyanates are eliminated in the practical application of the process according to the present invention. However, partial monoisocyanate elimination may occur if, on completion of the reaction, the product according to the present invention is freed from excess diisocyanate by thin layer evaporation at elevated temperature (about 170° C.). For this reason, it is advisable in cases where primary monoamines are used as starting materials to remove the excess, unreacted diisocyanate by reaction with suitable solvents, such as n-hexane. In cases where secondary monoamines are used as starting materials, there is no need for extraction to be carried out because, in this case, the elimination of monoisocyanate is precluded by the different structure of the reaction products.

In the practical application of the process according to the present invention, the properties of the modified polyisocyanates obtained, particularly the NCO functionality, the NCO-content and the viscosity thereof, may be controlled not only by selecting suitable starting materials, but also, and particularly easily, by adjusting the "degree of polyuretization", i.e. the number of NCO-groups consumed in the process per amino group reacted.

In the preferred use of secondary monoamines, particularly with aliphatically or cycloaliphatically bound amino groups, and aliphatic or cycloaliphatic diisocyanates, the preferred products according to the present invention corresponding to the above general formula are formed. In the particularly preferred use of dialkylamines containing $C_1$–$C_4$ alkyl radicals or of piperidine and of hexamethylene diisocyanate as starting materials in the practical application of the process according to the present invention, the particularly preferred products according to the present invention corresponding to the above general formula, wherein the radicals $R_1$ to $R_4$ correspond to the above definition of the particularly preferred starting materials and where n represents a number of from 2 to 8, are formed.

The products according to the present invention may be used, in particular, as an isocyanate component in the production of polyurethane plastics by the isocyanate-poly-addition process. They are suitable both for the production of polyurethane foams and also for the production of elastomers, coatings or bonds. Particularly when the products according to the present invention are used for the first of the above-mentioned applications, there is often no need for the excess diisocyanate to be distilled off on completion of the reaction according to the present invention.

The monomer-free products according to the present invention represent outstanding starting materials for the production of high-quality, weatherproof and light-stable lacquers. This applies, in particular, to those products according to the present invention which have been exclusively produced from aliphatic or cycloaliphatic starting materials.

The excellent compatibility of the products according to the present invention with standard commercial-grade polyhydroxy polyacrylates is particularly valuable for the use thereof as "lacquer isocyanates". Another advantage of the products according to the present invention over known biuret polyisocyanates is the fact that the products produced from secondary amines are stable with respect to monomer resplitting; in other words, there is no increase in the monomer content of the polyisocyanates according to the present invention, even during storage at elevated temperature (50° C.).

EXAMPLES

EXAMPLE 1

In a 4 liter, four-necked flask equipped with a stirrer, reflux condenser and contact thermometer, 135 g (3 mols) of dimethylamine were introduced under nitrogen into 3024 g (18 mols) of 1,6-diisocyanatohexane, the temperature in the reaction vessel rising to about 60° C. The corresponding urea was formed, passing into solution, except for some small residues, after addition of the amine. 7 g (0.19 mol) of hydrogen chloride in 100 g of 1,6-diisocyanatohexane were then added to the reaction mixture and the temperature increased to about 100° C. The NCO-content of the reaction solution, which was now clear, amounted to about 44% (corresponding to a consumption of 1 NCO-group per amino group). After 2 hours, the NCO-content had fallen to about 40% (corresponding to a consumption of 2 NCO-groups per amino group) and, after 4 hours, to 35% (corresponding to a consumption of about 3.3 NCO groups per amino group, corresponding to n=2.3). The reaction solution was cooled to 50° C. and 11 g (0.19 mol) of propylene oxide were added to bind the hydrolyzable chlorine. Subsequent thin-layer distillation gave 1600 g of 1,6-diisocyanatohexane as distillate and 1540 g of polyuretpolyisocyanate as residue (NCO-content=19.5%; viscosity at 25° C.=5000 mPa.s; residual content of monomeric 1,6-diisocyanatohexane=0.60%).

By monitoring the monomer content of product samples which had been stored over a prolonged period at 50° C., the polyisocyanate was found to be stable with respect to monomer resplitting.

| Storage (in weeks) | 1,6-diisocyanatohexane (%) |
|---|---|
| — | 0.60 |
| 1 | 0.72 |
| 4 | 0.68 |
| 6 | 0.67 |

EXAMPLE 2

As in Example 1, 3024 g (18 mols) of 1,6-diisocyanatohexane were reacted with 225 g (5 mols) of dimethylamine in the presence of 7 g (0.19 mol) of hydrogen chloride. After 7 hours, the NCO-content of the reaction mixture amounted to 27.4% (corresponding to a consumption of 3 NCO-groups per amino group (n=2)). In addition to 1000 g of 1,6-diisocyanatohexane, thin-layer evaporation gave 2150 g of polyuret polyisocyanate (NCO-content=16.2%; viscosity at 25° C.=30,000 mPa.s; residual monomer content=0.3%).

EXAMPLE 3

As in Example 1, 1008 g (6 mols) of 1,6-diisocyanatohexane were reacted with 45 g (1 mol) of dimethylamine in the presence of 3 g (0.08 mol) of hydrogen chloride. After 6 hours, the NCO-content of the reaction mixture had fallen to 28% (corresponding to a conversion of 5 NCO-groups per amino group (n=4)). The crude polyuretpolyisocyanate had a viscosity of 200 mPa.s/25° C.

EXAMPLE 4

The reactions summarized in the following Table were carried out in the same way as in Example 1:

| Isocyanate g (mols) | Amine g (mols) | Isocyanate/amine molar ratio | Catalyst | Yield (g) of polyuret polyisocyanate | NCO (%) | η 25° C. (mPa.s) | Monomer content (%) | n |
|---|---|---|---|---|---|---|---|---|
| 3024 (18) HDI* | 387 (3) dibutylamine | 6:1 | 4 g HCL | 1670 | 17 | 1400 | 0.68 | 2.3 |
| 3024 (18) HDI | 81 (2.6) methyl amine | 7:1 | 4 g HCl | 1340 | 19.5 | 9500 | 0.50 | 2.3 |
| 3024 (18) HDI | 117 (2.6) ethyl amine | 7:1 | 4 g HCl | 1390 | 19.3 | 6500 | 0.40 | 2.2 |
| 1008 (6) HDI | 85 (1) piperidine | 6:1 | 3 g HCl | 430 | 17.4 | 6500 | 0.45 | 2.1 |
| 3024 (18) HDI | 135 (3) dimethyl amine | 6:1 | 19 g methane sulphonic acid | 1430 | 17.4 | 11000 | 0.31 | 2.5 |
| 1008 (6) HDI | 45 (1) dimethyl amine | 6:1 | 7 g dimethyl amine hydrochloride | 500 | 18.4 | 7000 | 0.53 | 2.2 |
| 2260 (10) X** | 75 (1.67) dimethyl amine | 6:1 | 4 g HCl | 1010 | 14.3 | 4000 | 0.70 | 2.0 |
| 1776 (8) IPDI*** 672 (4) HDI | 90 (2) dimethyl amine | 6:1 | 3 g HCl | 1200 | 17 | 1600**** | 0.62 | 2.1 |

Key to the Table of Example 4
*HDI corresponds to 1,6-diisocyanatohexane
**X corresponds to 6-isocyanatocaproic acid-2-iso-cyanatoethyl ester
***IPDI corresponds to 3-isocyanatomethyl-3,5,5-trimethyl cyclohexyl isocyanate
**** in ethyl glycol acetate/xylene (1:1).

EXAMPLE 5

Following the addition of 1 g of a tertiary amine as catalyst and 0.4 g of cellulose butyrate propionate as levelling agent, 154 g of a 65% solution of a strongly branched polyester based on phthalic acid anhydride and trimethylol propane (hydroxyl content 8%) in ethyl glycol acetate/xylene (1:1) were diluted with 220 g of a solvent mixture of methylethyl ketone, butyl acetate, ethyl glycol acetate and toluene (4:1:4:1). 135 of a 75% solution of the polyisocyanate of Example 1 in ethyl glycol acetate/xylene (1:1) were then added (NCO/OH-molar ratio=1:1). The final lacquer solution was then applied to steel plates where the lacquer films hardened at room temperature. The hardened clear lacquer films were scratch-resistant, elastic and resistant to solvents, such as toluene, ethyl glycol acetate, ethyl acetate or acetone. They also had the following properties:

Layer thickness: approx. 50μ
Erichsen indentation (DIN 53 156)
after 2 days: 8.8 mm
after 5 days: 8.5 mm
after 14 days: 8.4 mm
Pendulum hardness (DIN 53 157)
after 2 days: 215 seconds
after 5 days: 225 seconds
after 14 days: 223 seconds.

EXAMPLE 6

154 g of the polyester solution described in Example 5 were ground with 100 g of titanium dioxide (rutile) to form a paste. In addition to catalyst and levelling agent, 120 g of the above-described solvent mixture described in Example 5 were added to this paste. 135 g of a 75% solution of the polyisocyanate of Example 1 in ethyl glycol acetate/xylene (1:1) were added to the thus-obtained mixture which was then thinly applied to steel plates. The pigment-containing lacquer films hardened at room temperature. They were distinguished by the scratch resistance and solvent resistance thereof and, compared with the clear lacquer films, had the following properties:

Layer thickness approx. 50μ
Erichsen indentation (DIN 53 156)
after 2 days: 9.1 mm
after 6 days: 8.5 mm
after 14 days: 8.9 mm
Pendulum hardness (DIN 53157)
after 2 days: 175 seconds
after 5 days: 180 seconds
after 14 days: 179 seconds Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for the production of modified organic polyisocyanates containing triuret or higher polyuret groups, wherein secondary monoamines are reacted with excess quantities of organic diisocyanates with formation of triuret or higher polyuret groups and with incorporation into the resulting product of the residue of the amine which is inert with respect to the reaction, the reaction being conducted in the presence of a proton-eliminating acid catalyst which is capable of reacting with isocyanate groups to form a mixed carbamic acid anhydride.

2. A process as claimed in claim 1, wherein aliphatic or cycloaliphatic monoamines or mixtures thereof are used as the monoamines.

3. A process as claimed in claims 1 or 2, wherein aliphatic and/or cycloaliphatic diisocyanates are used as organic diisocyanates.

4. A modification of the process claimed in claim 1, wherein, instead of the monoamines, reaction products of the monoamines and organic diisocyanates containing urea and/or biuret groups and the amine residue inert to the reaction with organic diisocyanates are used.

5. Compounds corresponding to the following general formula:

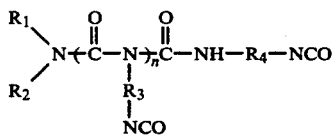

wherein

R$_1$ and R$_2$, which may be the same or different, each represents an aliphatic hydrocarbon radical containing from 1 to 20 carbon atoms or a cycloaliphatic hydrocarbon radical containing from 4 to 20 carbon atoms, or the two radicals together with the nitrogen atom may form a 5- or 6-membered heterocyclic ring optionally containing further hetero atoms selected from the group consisting of nitrogen sulfur and oxygen;

R$_3$ and R$_4$, which may be the same or different, each represents an aliphatic or cycloaliphatic hydrocarbon radical containing from 4 to 20 carbon atoms; and n represents a number of from about 2 to 8.

6. Compounds corresponding to the formula in claim 5 wherein

R$_1$ and R$_2$, which may be the same or different, each represents an aliphatic hydrocarbon radical containing from 1 to 4 carbon atoms or, together with the nitrogen atom, form a piperidine ring;

R$_3$ and R$_4$, each represents a hexamethylene radical; and n represents a number of from about 2 to 8.

7. In a process for the production of polyurethane plastics by the isocyanate-polyaddition process, the improvement comprising reacting modified organic polyisocyanates produced by the process of claim 1 with active hydrogen-containing compounds.

8. The compounds of claim 5 wherein the NCO-content is from about 10 to 22% by weight.

9. A process for the production of modified organic polyisocyanates containing triuret or higher polyuret groups comprising reacting:
(a) compounds selected from the group consisting of secondary monoamines and reaction products of secondary monoamines and organic diisocyanates containing urea or biuret groups, and
(b) excess organic diisocyanate in the presence of a proton-eliminating acid catalyst which is capable of reacting with isocyanate groups to form a mixed carbamic acid anhydride, wherein the residues of said monoamines which are inert with respect to said process are incorporated into the resulting product of said process.

10. The process of claim 9 wherein component (a) is a secondary monoamine.

11. The process of claim 10 wherein components (a) and (b) are present in an NCO/NH molar ratio of from about 5.5:1 to 100:1.

12. The process of claim 9 wherein the proton-eliminating acid catalyst is present in from about 0.001 to 10% by weight, based on the total weight of the reactants.

13. The process of claim 9 wherein the proton-eliminating acid catalyst is present in the form of a mixed carbamic acid anhydride, the corresponding ammonium salt of the proton-eliminating acid or mixtures thereof.

14. A process for the production of modified organic polyisocyanates containing triuret or higher polyuret groups comprising reacting compounds selected from the group consisting of secondary amines and reaction products of secondary amines and organic diisocyanates containing urea or biuret groups, with excess organic diisocyanate in the presence of a proton-eliminating acid catalyst which is capable of reacting with isocyanate groups to form a mixed carbamic acid anhydride, said excess organic diisocyanate being sufficient to provide an NCO/NH molar ratio of from about 5.5:1 to 100:1.

* * * * *